(12) United States Patent
Voelker

(10) Patent No.: US 11,202,020 B2
(45) Date of Patent: Dec. 14, 2021

(54) LENS SYSTEM FOR A CAMERA OBJECTIVE, CAMERA OBJECTIVE AND METHOD FOR PRODUCING A LENS SYSTEM

(71) Applicant: Carl Zeiss AG, Oberkochen (DE)

(72) Inventor: Benjamin Voelker, Dewangen (DE)

(73) Assignee: Carl Zeiss AG, Oberkochen (DE)

( * ) Notice: Subject to any disclaimer, the term of this patent is extended or adjusted under 35 U.S.C. 154(b) by 0 days.

(21) Appl. No.: 17/006,823

(22) Filed: Aug. 29, 2020

(65) Prior Publication Data
US 2021/0067713 A1    Mar. 4, 2021

(30) Foreign Application Priority Data

Aug. 29, 2019  (DE) .................... 10 2019 213 045.3

(51) Int. Cl.
| | |
|---|---|
| *G02B 1/11* | (2015.01) |
| *H04N 5/33* | (2006.01) |
| *H04N 5/225* | (2006.01) |
| *A61N 7/00* | (2006.01) |
| *A63F 9/06* | (2006.01) |

(52) U.S. Cl.
CPC ............... *H04N 5/332* (2013.01); *G02B 1/11* (2013.01); *H04N 5/2254* (2013.01); *A61N 2007/006* (2013.01); *A63F 2009/063* (2013.01); *A63F 2009/0629* (2013.01); *H01J 2211/44* (2013.01); *H01J 2329/892* (2013.01); *H01J 2329/897* (2013.01)

(58) Field of Classification Search
USPC ........................................................ 348/164
See application file for complete search history.

(56) References Cited

U.S. PATENT DOCUMENTS

| | | | |
|---|---|---|---|
| 11,086,114 B2* | 8/2021 | Wald ................. | G02B 21/0072 |
| 2004/0233411 A1* | 11/2004 | Shiraishi ........................ | 355/67 |
| 2013/0155314 A1* | 6/2013 | Wang ...................... | G02B 9/60 |
| | | | 348/360 |
| 2016/0004046 A1* | 1/2016 | Asami .................... | G02B 13/04 |
| | | | 359/713 |

* cited by examiner

*Primary Examiner* — Behrooz M Senfi
(74) *Attorney, Agent, or Firm* — Falk Ewers; Ewers IP Law PLLC

(57) ABSTRACT

A lens system for a camera objective has a plurality of optical lenses that are arranged one after another along an optical axis and are configured for imaging in the visually perceivable spectral range. At least a part of the optical lenses has two types of lens faces that intersect a beam path of the camera objective. At least three of said lens faces are provided with a first anti-reflective coating which has a larger reflectance in at least one partial region of the visible spectral range than a second anti-reflective coating of the remaining lens faces. In addition, a camera objective including the lens system and a method for producing a lens system are provided.

19 Claims, 2 Drawing Sheets

LENS SYSTEM FOR A CAMERA OBJECTIVE, CAMERA OBJECTIVE AND METHOD FOR PRODUCING A LENS SYSTEM

CROSS REFERENCE TO RELATED APPLICATIONS

This application claims priority to German patent application DE 10 2019 213 045.3, filed Aug. 29, 2019, the entire content of which is incorporated herein by reference.

TECHNICAL FIELD

The disclosure relates to a lens system for a camera objective, for example a camera objective for film recordings. The disclosure furthermore relates to such a camera objective. Moreover, the disclosure relates to a method for producing a lens system.

BACKGROUND

A camera objective ("objective" for short) is typically understood to mean an approximately cylindrical component of film or still cameras that typically has an optical unit, in particular a lens system formed from a plurality of optical lenses, i.e., lenses for imaging light in the visually perceivable spectral range (i.e., in particular a wavelength between 380 and 780 nanometers). In principle, mirror optical units or combinations of mirrors and lenses are also possible and known.

A goal when designing and producing objectives and the lens systems thereof is always to produce imaging with as few imaging aberrations as possible. Imaging aberrations include longitudinal and lateral chromatic aberrations that result, amongst other things, in undesirable color fringes in the imaged representation, spherical aberrations, so called distortions that result in barrel-type or pincushion-type distortions of straight lines, and the like. However, reflections at the lens faces that are transverse to the light-ray direction also result in imaging aberrations which are called, among other things, lens reflections, glares, "lens flares" or "ghosts". It is another goal when designing and producing objectives to ensure the transmission through the entire optical unit, i.e., in particular the lens system, is as large as possible so as to keep light losses in the imaged representation as low as possible. As a result, what is known as the light intensity of the relevant objective is likewise kept high so that recordings can be taken even if the exposure is comparatively poor or in the case of light conditions with low illumination values, for example at night, in rooms without additional illumination and the like.

In order to obtain the highest possible transmission values, the proportion of the light reflected at the optical faces (in particular the interfaces of the lenses) must accordingly be kept low. To this end, the lenses are provided with an "optical coating" in modern objectives, in particular with coatings that reduce reflection. In the case of lens faces forming in particular a glass-air interface, coatings having a plurality of layers of different materials with correspondingly different refractive indices are typically used. This suppresses or at least largely reduces reflections at said faces, which means that the highest possible proportion of the incident light is actually transmitted (in particular all the way to the image sensor of the relevant camera).

On the other hand, it is sometimes also of interest to users to include visible reflections in the imaged representation, for example to better convey moods, to be able to indicate glaring light and the like. This is an area of conflict with the light intensity because the transmission is intended to be as great as possible even in that case.

SUMMARY

It is an object of the disclosure to provide a camera objective with the best possible transmission behavior while still imaging visible reflections.

The object is achieved by a lens system for a camera objective, a camera objective having a lens system, and a method for producing a lens system as described herein.

The lens system according to an aspect of the disclosure serves for use in a camera objective, in particular in the camera objective according to an aspect of the disclosure.

For this purpose, the lens system has a plurality of optical lenses that are arranged one after the other along an optical axis and are configured for imaging in the visually perceivable spectral range. The lenses are in particular lenses made from glass. At least a part of the optical lenses in this case has two lens faces that intersect a beam path of the camera objective (formed with the lens system). At least three lens faces of the lens system are here provided with a first anti-reflective coating which has a larger reflectance, i.e., reflectivity, in at least one partial region of the visible spectral range (in particular in a targeted manner) than a second anti-reflective coating with which the remaining lens faces are provided.

This first anti-reflective coating, which reflects more strongly than the second anti-reflective coating, specifically because at least three lens faces are provided in this way, makes at least two multiple reflections (in particular double reflections) that are visually perceivable in the imaged representation possible. In particular, light is thus reflected at one of the lens faces that are coated in this way (typically in the direction of an object-side, first lens surface, which is known as the front face, of the lens system) and again at a further lens face having such a coating in the direction of the image side (i.e. in the direction of the image-side exit lens face). Using at least three lens faces that are coated in this way makes it possible here that the intensity of the double reflection in the imaged representation is increased for visual perception, in particular for an image of the double reflection that is subjectively perceived as appealing or artistically pleasing.

An "anti-reflective coating" here and below is understood to mean in particular a coating that has at least one layer of material and significantly influences the ratio of transmission to reflection at the coated surface. Such an anti-reflective coating is typically formed such that the transmission can be increased (and consequently the reflection decreased) by at least 0.25 percent, typically by at least 0.5 percent, as compared to a lens that is uncoated or coated only with what is known as a hard coating (used in particular for scratch resistance). The (first and second) anti-reflective coating is thus not a hard coating.

The term "glass" is used here and in the text below for the sake of simplicity both for mineral glass and for "organic" glass, i.e., including for transparent (or "optical") plastic. Consequently, the respective lens can be made from a crown glass, a borosilicate glass or the like, and from a plastic, for example a polymethyl methacrylate (PMMA), a cyclic olefin copolymer (COC), a polycarbonate (PC), a polyallyl diglycol carbonate (PADC) or the like.

The camera objective according to an aspect of the disclosure includes the lens system described here and below and also an objective tube (also referred to as the outer housing), in which the lens system is enclosed against the ingress of impurities into the beam path (i.e., in particular against ingress of impurities between the lenses). For example, the objective tube here carries the lens system directly or indirectly via an additional inner objective tube (also known as a lens mount) and optionally also has setting means (e.g., rotating rings) for adjusting a variable stop arranged in the beam path and/or at least one focus and/or zoom lens group of the lens system. Consequently, the camera objective equally has all the features and advantages of the lens system.

The method according to an aspect of the disclosure serves for producing the lens system described here and below. Initially, the optical lenses configured for imaging in the visual spectral range are arranged one after the other along the optical axis to form the beam path of the camera objective. At least part of the optical lenses here has the two lens faces intersecting the beam path. Furthermore, at least three lens faces are provided with the first anti-reflective coating to produce the at least one multiple reflection (typically at least two double reflections) visible in the imaged representation. As described above, this first anti-reflective coating has a higher reflectance (i.e., a larger reflectivity) in at least one partial region of the visible spectral range (in particular in a targeted manner) as compared to the second anti-reflective coating of the remaining lens faces.

The method according to an aspect of the disclosure thus leads to the same advantages and physical features as were described in connection with the lens system. Accordingly, the lens system also has features and advantages that may have been described in connection with the method for producing the lens system.

In principle, each lens has two optically effective interfaces (i.e., interfaces influencing the beam path) that can also be coated against reflections. Said interfaces can form (in particular independently of any coating that may be present) a transition from glass to air or—in particular in the case of cemented lenses, for example in the case of an achromatic or apochromatic lens—from glass to glass (typically from one type of glass to another; usually by interposing a "cement", possibly also a coating). However, the interfaces referred to here and below as lens faces are typically glass-air interfaces specifically. Said interfaces are thus situated at locations in the region of the beam path at which a lens body and an air space—for example the environment or an air gap between two lenses—follow one another, even if more specifically the pure ("bare") surface of the respective lens in the final finished state is delineated from the corresponding air space by the first or second anti-reflective coating (and possibly also a hard layer).

The lens faces provided with the first anti-reflective coating can be arranged both at the front sides extending in an intended direction of the light along the beam path and at the rear sides of the lenses. Reflections of a light ray that is incident on the respective lens from the object side or that passes through the lens can thus be brought about in a targeted manner at transitions from air to glass (i.e., on the entry side) or from glass to air (i.e., on the exit side to the respective lens).

The number of the lens faces coated with the first anti-reflective coating is typically smaller than the number of the lens faces that are present. With particular preference, the number of the lens faces coated with the first anti-reflective coating is also smaller than the number of the lens faces coated with the second anti-reflective coating. As a result, the reflection of the overall system is advantageously kept as small as possible and thus a comparatively high transmission is made possible.

With particular preference, the number of the lens faces having the first anti-reflective coating lies between 25 and 60 percent, typically between 28 and 55 percent, of the total number of lens faces. This allows for the double reflections caused in the imaged representation by the lens faces that are coated in this manner to be (in particular subjectively) easily visible yet not (yet) subjectively bothersome and for a high transmission to be nevertheless possible. In particular, the imaged double reflections are in this case not so pronounced that information perceived as being important is lost in the imaged representation, for example is covered or superposed (in particular overexposed, i.e., "clipping" of an image sensor of a camera carrying the objective).

In one variant, the lens system is formed with a wide-angle focal length (i.e., in particular for conveying a wide-angle impression). The value of the focal length from which the lens system has such wide-angle properties is here in particular dependent on what is known as an image circle that can be exposed by the lens system on the image plane and optionally on the image format (in particular the format of the image sensor to be exposed) of the camera. In the case of an example of an image circle with a radius of 21.62 mm (which is used in particular for an image sensor in the "small frame" or "full frame" format), the lenses are designed and arranged for the wide-angle properties in particular such that a focal length of the lens system is less than or equal to 40 millimeters. For other image circle values and/or image formats or formats of image sensors, the maximum focal length for wide angles are correspondingly scaled as appropriate. In the case of the wide-angle focal length, the number of the lens faces having the first anti-reflective coating is typically selected at between 30 and 54 percent (i.e., at least 30 and at most 54 percent) of the total number of the lens faces (in particular without taking account of any glass-glass interfaces that may be present, for example in achromatic or apochromatic lenses).

In an alternative variant, the lens system has a tele focal length. In the case of the example of the previously described image circle or format, the lenses are in particular designed and arranged such that a focal length of more than 40 millimeters (for example larger than a focal length that is typically referred to as a "normal focal length") is obtained. In the case of the tele focal length, the number of the lens faces having the first anti-reflective coating lies between 33 and 44 percent of the total number of lens faces.

In an exemplary embodiment, in particular five to fourteen, typically six to twelve, lens faces having the first anti-reflective coating are present in the lens system, typically in the case of 12 to 18 individual lenses.

In an exemplary embodiment, a location (or: position) of the respective lens face carrying the first anti-reflective coating along the optical axis is selected in dependence on one or more criteria (or: "parameters"). A criterion that is used in this case is a target manifestation of the respective multiple reflection (double reflection) in the imaged representation, a type of glass selected for the relevant lens (e.g., high refractive index or low refractive index), a curvature of the lens face (i.e., whether said lens face is convex or concave), a radius of curvature of the lens face, a lens diameter and/or a location of the lens face in the beam path (in particular in relation to neighboring lenses). As part of the method for producing the lens system, typically the target manifestation of the respective multiple reflection is initially "selected", specified as the "target" for the imaging properties of the lens system and then additionally the location of the respective lens face having the first anti-reflective coating is selected in dependence on at least one of the aforementioned criteria.

A further criterion that is likewise taken into account in any case is expediently setting of as high a total transmittance of the lens system as possible, specifically as compared to a lens system equipped only with lens faces provided with the second anti-reflective coating. The locations of the lens faces provided with the first anti-reflective coating are typically chosen such that the difference between a purely geometric (minimum) stop number (also referred to as "f-stop"; in particular the ratio of focal length to entrance pupil, also: "aperture", of the lens system) and a stop number that refers to the transmission of the system (also called "T-stop"; in particular the ratio of the geometric stop number to the square root of the transmittance) is up to 2 stop values (i.e., 0.2) at least in light-intense objectives (i.e., with a minimum geometric stop number of up to 2.0). An objective having an f-stop of 1.4 thus typically has a T-stop of "only" 1.6 despite the use of the first anti-reflective coating. Such a low overall reflection is attained here in particular through a combination of the number of the lenses having the first anti-reflective coating and through taking into account the above-described criteria.

In particular a desired image of the multiple reflection or of the respective multiple reflection in the imaged representation is used as the target manifestation of the respective multiple reflection. This is influenced in turn by various factors, in particular the geometric shape (or structure), the intensity (possibly an intensity profile), a delineation that is spatially more or less sharp (also referred to as focusing of the reflection), a (possibly dominating) color and/or a color profile. For example circles, polygons, ovals (in each case in particular as two-dimensional spots or rings), structures that convey a three-dimensional impression (for example seem like a sphere, a drop or a torus) and/or "light rays" (in particular lines or bundled lines) that, owing to a high degree of focusing, appear to be for example sharply delineated locally and to be highly luminous by comparison or lie like a veil (frequently with comparatively low luminosity) over a relatively large area of the imaged representation are imaged as the geometric shape.

In particular, the respective target manifestation is chosen under subjective, for example artistic or design (possibly application-specific), aspects, in particular whether the respective multiple reflection is perceived on the basis of its target manifestation more as bothersome (for example because of a perceived glare or superposition of other elements of the imaged representation) or as pleasant and "conducive" to the image impression. For example, comparatively strongly focused structures are perceived to be more suitable than large-area, defocused structures with a high intensity that can result in superposition of the actual constituent parts of the imaged representation (i.e., in particular "useful information") or even in the destruction of said useful information by overexposure. Consequently, the optical effect of the respective multiple reflection can optionally also advantageously be set to customers' specifications.

For selecting the location of the respective lens face provided with the first anti-reflective coating, optics simulation software is used with particular preference to approximate the actual manifestation (or at least the manifestation expected based on the simulation) of the respective multiple reflection to the previously selected target manifestation. In particular, the imaged representation—for example of a light source—that is producible with the lens system, and thus also the respective multiple reflection, is thus typically presented by way of a simulation. Depending on the above-described criteria, the correspondingly coated lens faces are then distributed (positioned) until the desired result is achieved.

In particular, the location of the respective lens face carrying the first anti-reflective coating along the optical axis is then in particular selected (typically on the basis of the above criteria) such that the highest possible transmission with simultaneous artistically appealing manifestation of the respective multiple reflection is attained.

In an exemplary embodiment that is in principle conceivable as part of the disclosure, the first anti-reflective coating has a higher reflectivity over the entire visible spectral range than the second anti-reflective coating.

In an exemplary embodiment, however, the first anti-reflective coating is chosen such that light of the hue intended for the respective multiple reflection (i.e., of a selected partial region of the visible spectral range that is narrower than the entire visible spectral range) is reflected while other hues are transmitted in particular in order to set a hue for the multiple reflection or the respective multiple reflection. In the reverse, this means that light of a selected partial region of the visible spectral range that is narrower than the visible spectral range is transmitted at a higher proportion than light of at least another partial region of the visible spectral range, in particular of the partial region that is intended for the respective multiple reflection. Thereby, the optical effect of the respective multiple reflection can advantageously also be set to customers' specifications.

Typically, the first anti-reflective coating in the above case is chosen such that light from the range of the red hues (in particular of the red-relation part of the visible spectral range) is transmitted at a higher proportion compared to other partial regions (i.e., in particular other hues, for example blue hues). The first anti-reflective coating is to this end formed in particular on the respective lens face by a first coating variant that has a reflectance profile with a minimum between 585 and 635 nanometers, typically of around 610 nanometers. That means that in the case of the first coating variant, light having a wavelength in the region of the minimum is transmitted better (that is to say at a higher proportion) than light having the wavelengths outside the minimum (with respect to a curve of the reflectance profile in particular outside the "trough" edges delimiting the minimum). Alternatively, the first anti-reflective coating is formed by a second coating variant that has a reflectance profile with a minimum between 635 and 685 nanometers, typically of around 660 nanometers. Optionally, both coating variants are used on different lens faces in the same lens system. Owing to the reflectance profile thus selected of the first anti-reflective coating, specifically of the two coating variants, light in particular in the blue partial region is thus more strongly reflected than light in the red partial region of the visible spectral range. As a result, the hue of the respective multiple reflection is "moved" to the blue partial region of the visible spectral range and, in addition, a "warmer" color impression of the entire imaged representation (i.e., a higher "color temperature") is conveyed owing to the red partial region that is transmitted at a comparatively higher proportion.

In an optional development, at least one of the afore-described minima is set such that the reflectance in the region of said minimum is close to the reflectance of the second anti-reflective coating, that is to say is "only" slightly higher or comparatively small.

However, it is likewise possible in principle to choose a coating variant whose minimum in the reflectance profile lies for example in the yellow or blue partial region of the visible spectral range so as to obtain multiple reflections of a corresponding different color.

In an exemplary embodiment, the number of the lens faces with the second coating variant is larger in the case of the tele focal length than the number of the lens faces with the first coating variant. Optionally, only lens faces coated with the second coating variant (in addition to the lens faces provided with the first anti-reflective coating) are present here.

In the case of the wide-angle focal length, by contrast, there are in particular more lens faces with the first coating variant than with the second coating variant.

The lens system typically has at least two lens groups arranged one behind the other along the optical axis. The division of all lenses into said two lens groups thus typically takes place here at an air gap that is typically variable for an adjustment of an imaging property, in particular a focus position, within the beam path. The adjustment of the "thickness" of the air gap is here effected by a lens (or lens group, in particular also called "focus lens" or "focus group") that is typically arranged on the image side with respect to said air gap and is displaceable at least along the optical axis. The lens group that is arranged on the object side with respect to said variable air gap is referred to here and below as "front group", and the lens group arranged on the image side with respect to said air gap is referred to here and below as "back group". The back group also includes, as part of the convention used here and below, in particular the displaceable lens or lens group.

In an exemplary embodiment, the number of the lens faces with the first anti-reflective coating within the front group in the case of the wide-angle focal length is larger than within the back group.

For the case of the tele focal length, by contrast, the number of the lens faces with the first anti-reflective coating within the back group is typically larger than within the front group.

In a further exemplary embodiment, the first anti-reflective coating on a lens made of a type of glass with a comparatively high refractive index has a lower number of layers than on a lens made from a type of glass with a lower refractive index. In other words, the first anti-reflective coating on a high-refractive type of glass is made up by a lower number of layers than on a low-refractive type of glass.

As an example of a lens system with a wide-angle focal length of 25 millimeters (in particular in a lens system for full frame), 30 percent of the lens faces are covered with the first anti-reflective coating. Five lens faces having the first coating variant and three lens faces having the second coating variant are used here. Four lens faces having the first anti-reflective coating are concave, and the rest are convex. In addition, six of the lens faces having the first anti-reflective coating are located in the front group, one in the back group upstream of a variable (system) stop, and one downstream of it.

As an example of a lens system with a tele focal length of 85 millimeters (in particular in a lens system for full frame), 33 percent of the lens faces are covered with the first anti-reflective coating, specifically of the second coating variant. Two of said lens faces are concave, and the rest are convex. Furthermore, all of said lens faces are located in the back group, with three located upstream of the variable stop and three lens faces downstream of it.

The conjunction "and/or" should here and below be understood to mean in particular that the features linked by this conjunction can be formed together and as alternatives of one another.

BRIEF DESCRIPTION OF THE DRAWINGS

The disclosure will now be described with reference to the drawings wherein.

DESCRIPTION OF EXEMPLARY EMBODIMENTS

Mutually corresponding parts are provided with the same reference signs throughout the figures.

Figure 1:
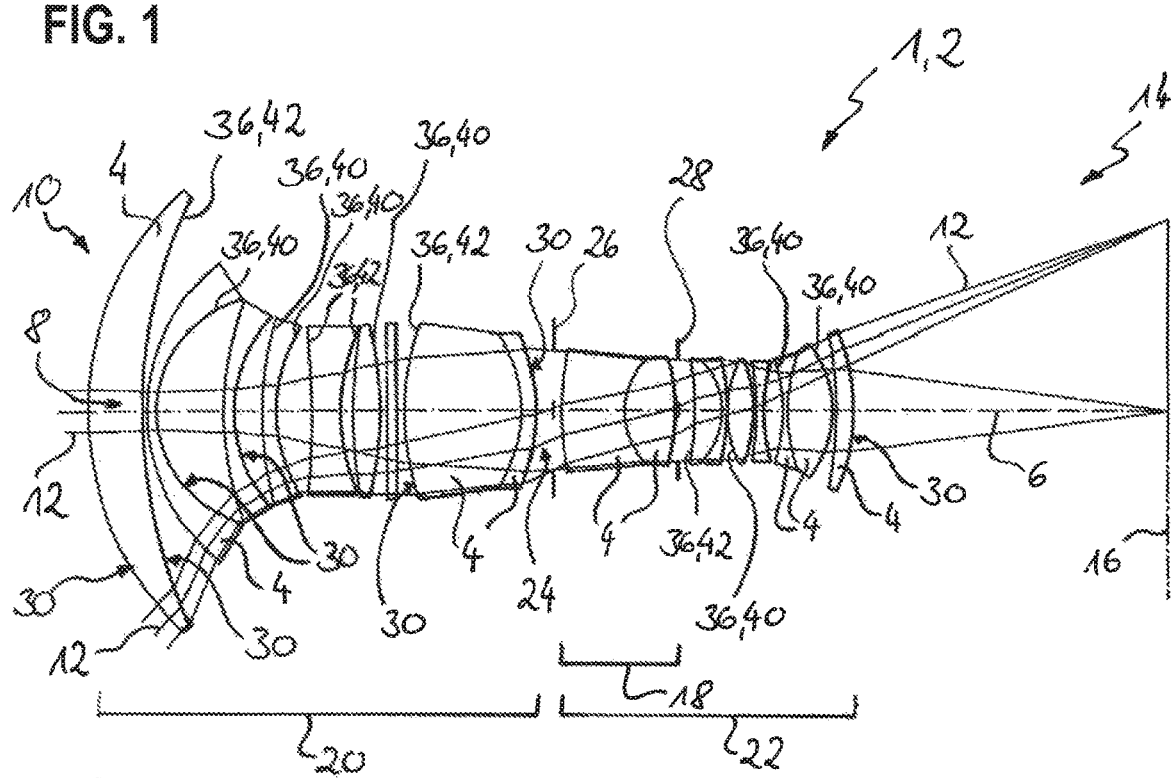
FIG. 1 shows a schematic side view of a lens system.
Figure 2:
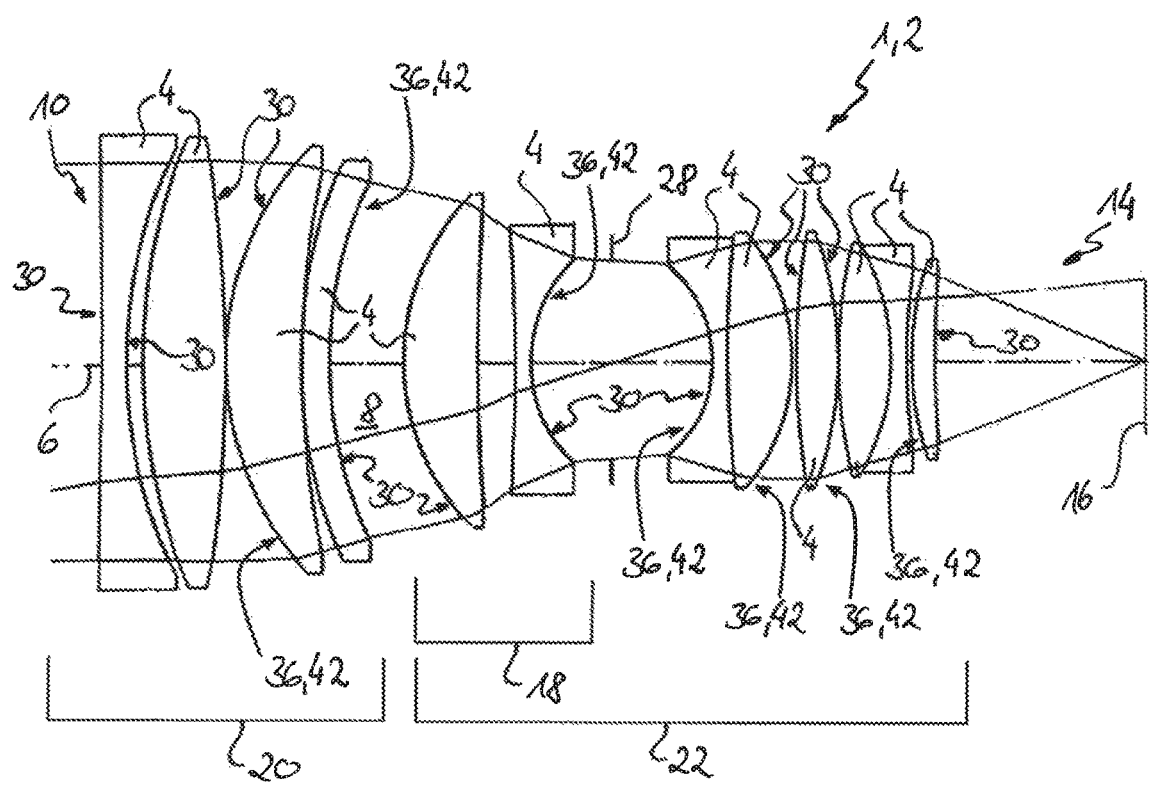
FIG. 2 shows a view of the lens system shown in FIG. 1 according to a further exemplary embodiment.

FIGS. 1 and 2 each schematically show an exemplary embodiment of a lens system 1 that is part of a camera objective (objective 2, for short). The lens system 1 includes a plurality of optical lenses 4 (for the sake of clarity, at least in FIG. 1 not all lenses are provided with reference signs) that are made from mineral glass, specifically in part from different types of glass (in an alternative exemplary embodiment, at least in part also from transparent plastic). The lenses 4 are here arranged along an optical axis 6 and are used to form a beam path 8 for light rays 12 that are incident from an object side 10. The light rays 12 are refracted by the individual lenses 4 and then imaged on an image side 14 onto an image plane 16, in this case in a focused manner. If the objective 2 is mounted to a camera, a film or an image sensor, in each case arranged in the image plane 16, is exposed here.

For focusing the light rays 12 at the image plane 16, the lens system 1 has a focus group 18, specifically formed in FIG. 1 by two lenses 4 cemented together, which are arranged displaceably relative to a "front group" 20 which is formed by the lenses 4 arranged on the object side. A corresponding mount of the objective 2 for the lenses 4 and adjustment means, and an outer housing are not illustrated in detail. The lenses 4 that are arranged following the front group 20 on the image side—including the focus group 18—are referred to as back group 22.

In the exemplary embodiment shown in FIG. 1, a coma stop 26 is arranged in an air gap 24, which is variable due to the adjustability of the focus group 18, between the front group 20 and the back group 22. The focus group 18 is followed on the image side by an adjustable stop that is referred to as the "system stop 28".

To avoid, or at least reduce, reflections of light rays 12 at the interfaces of the lenses 4 intersecting the beam path 8, at least the glass-air interfaces—referred to here as "lens faces 30" (only denoted in part for the sake of clarity)—are coated with an anti-reflective coating.

However, so as to not completely prevent multiple reflections, specifically what are known as double reflections 32 (see FIG. 3, also referred to as "lens flares") in an imaged representation 34, which are caused by a first reflection of a light ray 12 at a lens face 30 and a subsequent second reflection at a further lens face 30, more than three selected lens faces 30 are provided with a first anti-reflective coating. Said first anti-reflective coating has a reflectivity (i.e., a reflectance) that is set in a targeted manner and higher than the second anti-reflective coating used on the remaining lens faces 30. For this reason, these selected lens faces 30 are also referred to as "reflection faces 36" below.

Figure 3:
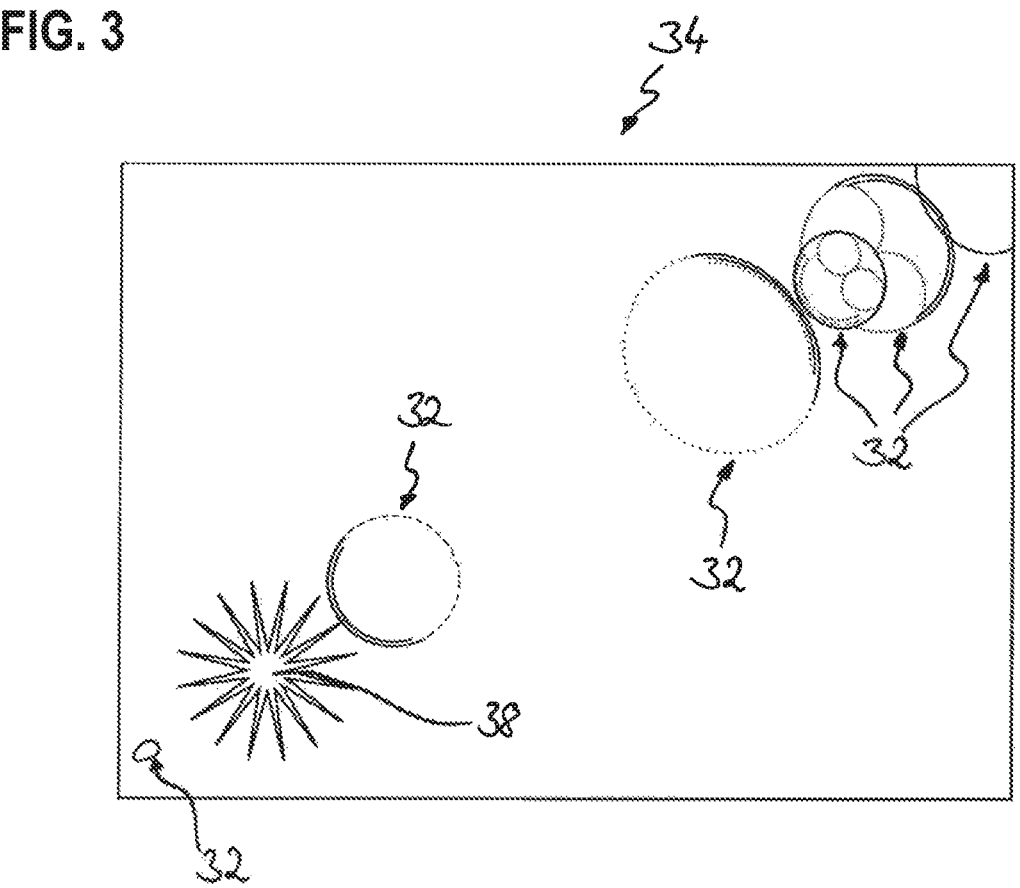
FIG. 3 shows a schematic view of imaging of a light source and of double reflections that occur in that case.

FIG. 3 illustrates various manifestations of double reflections 32 by way of example, which may also be desirable in the combination shown. The manifestations here have different structures (forms), different intensities, different focusing and the like. Around a light source 38, radiant structures that are comparatively strongly delineated (at least close to the light source 38) and bright (i.e., having a high intensity) and represent diffraction effects at the system stop 28 can be seen. To the left of the light source 38, an approximately drop-shaped spot can be seen as the double reflection 32. On the right side of the light source 38, various structures occur as double reflections 32 that are oval, two-dimensional or even give a three-dimensional impression (e.g., a type of torus in the region of the upper right-hand corner of the imaged representation 34). The structures of the individual double reflections 32 here also have intensity profiles that face or face away from the light source 38 (indicated by dashed, dash-dotted and solid lines).

So as to be able to set a desirable target manifestation of the double reflections 32, for example comparable to FIG. 3, while still having to accept the lowest possible reflection losses over the optical path through the lens system 1, more reflection faces 36 are arranged in the front group 20 than in the back group 22 in the case of a lens system 1 having a wide-angle focal length, as is schematically illustrated in FIG. 1. Specifically, eight reflection faces are arranged in the front group 20 and four reflection faces are arranged in the back group 22.

The selection of the respective lens faces 30 is made here on the basis of a simulation to approximate the actual manifestation of the double reflections 32 to the target manifestation.

So as to be able to influence the color effect of the respective double reflection 32, two coating variants are used that have a minimum in their reflectance profile in the red hue region (i.e., in the red partial region of the visible spectral range). These two coating variants are used with different numbers, depending, among other things, on the focal length of the lens system 1. A first coating variant 40 has the minimum at a wavelength of 610 nanometers, the second coating variant 42 has the minimum at 660 nanometers.

FIG. 2 shows the lens system 1 matched to a tele focal length, i.e., a focal length of more than 40 millimeters. In this case, more of the reflection faces 36 are used in the back group 22 and with a larger frequency the second coating variant 42. In the present exemplary embodiment, specifically only the second coating variant 42 is used.

The object of the disclosure is not restricted to the exemplary embodiments described above. Rather, further exemplary embodiments of the disclosure can be derived from the above description by a person skilled in the art. In particular the individual features of the disclosure described with reference to the various exemplary embodiments and the design variants thereof can also be combined in another way.

LIST OF REFERENCE NUMERALS

1 Lens system
2 Objective
4 Lens
6 Optical axis
8 Beam path
10 Object side
12 Light ray
14 Image side
16 Image plane
18 Focus group
20 Front group
22 Back group
24 Air gap
26 Coma stop
28 System stop
30 Lens face
32 Double reflection
34 Imaged representation
36 Reflection face
38 Light source
40 Coating variant
42 Coating variant

What is claimed is:

1. A lens system for a camera objective, the lens system comprising:
   a plurality of optical lenses arranged one after another along an optical axis thereby forming a beam path, and configured for imaging in a visually perceivable spectral range;
   at least a part of the plurality of optical lenses having lens faces which intersect the beam path of the camera objective;
   the lens faces forming a first group of lens faces and a second group of lens faces;
   the first group of lens faces including at least three of the lens faces and being provided with a first anti-reflective coating having a first reflectance in at least one partial region of a visible spectral range;
   the second group of lens faces being provided with a second anti-reflective coating having a second reflectance in the at least one partial region of the visible spectral range;
   the first reflectance being larger than the second reflectance.

2. The lens system according to claim 1, wherein the lens faces are glass-air interfaces.

3. The lens system according to claim 1, wherein the first group of lens faces having the first anti-reflective coating includes between 25 and 60 percent of a total number of the lens faces.

4. The lens system according to claim 1, wherein the first group of lens faces having the first anti-reflective coating includes between 28 and 55 percent of a total number of the lens faces.

5. The lens system according to claim 3, having a wide-angle focal length, and
   wherein the first group of lens faces having the first anti-reflective coating includes between 29 and 55 percent of the total number of the lens faces.

6. The lens system according to claim 3, having a tele focal length, and
   wherein the first group of lens faces having the first anti-reflective coating includes between 33 and 44 percent of the total number of the lens faces.

7. The lens system according to claim 1, wherein the first group of lens faces having the first anti-reflective coating includes five to fourteen of the lens faces.

8. The lens system according to claim 1, wherein the first group of lens faces having the first anti-reflective coating includes six to twelve of the lens faces.

9. The lens system according to claim 1, wherein a location of a lens face carrying the first anti-reflective coating along the optical axis is selected depending on at least one of:
- a target manifestation of a multiple reflection in an imaged representation,
- a type of glass selected for the respective lens,
- a curvature of the lens face,
- a radius of the curvature of the lens face,
- a lens diameter, and
- the location of the lens face in the beam path.

10. The lens system according to claim 1, wherein the first anti-reflective coating is formed such that light of a selected partial region of the visible spectral range is reflected at a higher proportion than light of a further spectral range.

11. The lens system according to claim 10, wherein the first anti-reflective coating is formed on a respective lens face by at least one of:
  (a) a first coating variant having a first reflectance profile with a minimum between 585 and 635 nanometers, typically of around 610 nanometers, or
  (b) a second coating variant having a second reflectance profile with the minimum between 635 and 685 nanometers, typically of around 660 nanometers.

12. The lens system according to claim 10, wherein the first anti-reflective coating is formed on a respective lens face by at least one of:
  (a) a first coating variant having a first reflectance profile with a minimum of around 610 nanometers, or
  (b) a second coating variant having a second reflectance profile with the minimum of around 660 nanometers.

13. The lens system according to claim 11, wherein, when the lens system has a tele focal length, a number of the lens faces with the second coating variant is larger than the number of the lens faces with the first coating variant.

14. The lens system according to claim 1, further comprising:
- a front group of lenses and a back group of lenses forming a variable air gap between the front group of lenses and the back group of lenses, the variable air gap being variable for an adjustment of an imaging property, the imaging property being a focus position;
- the front group of lenses being arranged on an object side with respect to the variable air gap;
- the back group of lenses being arranged on an image side with respect to the variable air gap, and
- when the lens system has a wide-angle focal length, a number of the lens faces with the first anti-reflective coating in the front group of lenses being larger than the number of the lens faces with the first anti-reflective coating in the back group of lenses.

15. The lens system according to claim 1, further comprising:
- a front group of lenses and a back group of lenses forming a variable air gap between the front group of lenses and the back group of lenses, the variable air gap being variable for an adjustment of an imaging property, the imaging property being a focus position;
- the front group of lenses being arranged on an object side with respect to the variable air gap;
- the back group of lenses being arranged on an image side with respect to the variable air gap, and
- when the lens system has a tele focal length, a number of the lens faces with the first anti-reflective coating in the back group of lenses is larger than the number of the lens faces with the first anti-reflective coating in the front group of lenses.

16. The lens system according to claim 1, wherein:
- the first anti-reflective coating on a first optical lens of the plurality of optical lenses made from a type of glass having a substantively high refractive index has a first number of layers,
- the first anti-reflective coating on a second lens made from the type of glass having a substantively low refractive index has a second number of layers, and
- the first number of layers is lower than the second number of layers.

17. The camera objective comprising:
- the lens system according to claim 1; and
- an objective tube in which the lens system is enclosed to prevent an ingress of impurities into the beam path.

18. A method for producing a lens system according to claim 1, the method comprising:
- arranging the plurality of optical lenses configured for imaging in the visually perceivable spectral range one after another along the optical axis to form the beam path of the camera objective, at least the part of the plurality of optical lenses having the lens faces which intersect the beam path, the lens faces forming the first group of lens faces and the second group of lens faces, the first group of lens faces including at least three of the lens faces; and
- for producing at least one multiple reflection which is visible in an imaged representation, providing the first group of lens faces with the first anti-reflective coating having the first reflectance in the at least one partial region of the visible spectral range and providing the second group of lens faces with the second anti-reflective coating having the second reflectance in the at least one partial region of the visible spectral range, and the first reflectance being larger than the second reflectance.

19. The method according to claim 18, further comprising:
- specifying a target manifestation of the at least one multiple reflection in the imaged representation, and
- selecting a location of a respective lens face carrying the first anti-reflective coating along the optical axis depending on at least one of:
- the target manifestation of the at least one multiple reflection in the imaged representation,
- a type of glass selected for a corresponding lens,
- a curvature of the lens face,
- a radius of curvature of the lens face,
- a lens diameter, and
- the location of the lens face in the beam path.

* * * * *